(12) United States Patent
Sisler et al.

(10) Patent No.: US 8,936,931 B2
(45) Date of Patent: Jan. 20, 2015

(54) METHODS AND APPARATUS OF CONTROLLING SURFACE WETTABILITY OF XEROGRAPHIC PRINTS

(75) Inventors: Gordon Sisler, St. Catharines (CA); Nicoleta Mihai, Oakville (CA); T. Brian McAneney, Burlington (CA); Valerie Farrugia, Oakville (CA)

(73) Assignee: Xerox Corporation, Norwalk, CT (US)

( * ) Notice: Subject to any disclaimer, the term of this patent is extended or adjusted under 35 U.S.C. 154(b) by 131 days.

(21) Appl. No.: 13/235,196

(22) Filed: Sep. 16, 2011

(65) Prior Publication Data

US 2013/0071912 A1    Mar. 21, 2013

(51) Int. Cl.
*B09C 1/10*        (2006.01)
*D21H 21/16*    (2006.01)
*G01N 13/02*    (2006.01)

(52) U.S. Cl.
CPC ............... *D21H 21/16* (2013.01); *G01N 13/02* (2013.01)
USPC ....................................................... 435/264

(58) Field of Classification Search
USPC ....................................................... 435/264
See application file for complete search history.

(56) References Cited

U.S. PATENT DOCUMENTS

| | | | | |
|---|---|---|---|---|
| 5,337,132 A | * | 8/1994 | Cherian | 430/126.1 |
| 5,605,881 A | * | 2/1997 | Machida et al. | 510/166 |
| 6,265,191 B1 | * | 7/2001 | Mizusawa et al. | 435/177 |
| 2002/0142452 A1 | * | 10/2002 | Yang et al. | 435/278 |
| 2006/0260772 A1 | * | 11/2006 | Raghukumar et al. | 162/5 |
| 2007/0021522 A1 | * | 1/2007 | Halfyard et al. | 522/18 |
| 2008/0014513 A1 | * | 1/2008 | Sisler et al. | 430/11 |
| 2010/0196682 A1 | * | 8/2010 | Mihai et al. | 428/212 |
| 2010/0196819 A1 | | 8/2010 | Song et al. | |

FOREIGN PATENT DOCUMENTS

EP    2163950    *    3/2010    ............. G03G 9/08

OTHER PUBLICATIONS

Tappi. Contact angle of water droplets on corona-treated polymer film surfaces. T 565 pm-96. 1996.*
Deng Y. Application of surfactant spray in flotation deinking. 1999. Institute of Paper Science and Technology, Atlanta, Georgia.*
Park et al. The effects of temperature and pH on enzyme kinetics. Fundamentals of Chemistry, John Wiley & Sons, Inc. 2000;1-4.*
Rame-hart. Glossary of surface science terms. Rame-hart Instrument Co. 2010;1-7.*

* cited by examiner

*Primary Examiner* — Ruth Davis
*Assistant Examiner* — Lynn Y Fan
(74) *Attorney, Agent, or Firm* — MH2 Technology Law Group LLP

(57) ABSTRACT

Exemplary embodiments provide methods and apparatus of using an enzyme-surfactant solution to control surface wettability of a xerographic print.

19 Claims, 4 Drawing Sheets

METHODS AND APPARATUS OF CONTROLLING SURFACE WETTABILITY OF XEROGRAPHIC PRINTS

BACKGROUND

In a typical electrostatographic reproducing apparatus, a light image of an original to be copied is recorded in the form of an electrostatic latent image upon a photosensitive member. The latent image is subsequently rendered visible by the application of electrostatically charged thermoplastic resin particles which are commonly referred to as toner. The developed image is then fixed to the imaging surface or is transferred to a receiving substrate, such as paper, to which it is fixed by a suitable fusing technique involving the application of heat, resulting in a xerographic print or toner-based printed substrate.

The xerographic print presents a complex array of surface energies and wetting responses. The surface energy of toner depends on its composition and in general varies from that of the paper to other substrate, which itself exhibits considerable variation depending on its composition, presence of coating, etc. Additionally in the case of xerographic print engines employing fuser oils, the surface energy of each component is altered by the level and nature of the fuser oils present, as well as the interaction between the oil, toner, and substrate. Finally, there is variable roughness and porosity associated with both toner (e.g., half-tone screens versus solids) and substrate, which affects the wetting response. The variability in surface energy and wetting response is measurable over a range of scales using familiar techniques involving sessile drop contact angles.

There are many situations where it is desirable to modify xerographic print surfaces to be less hydrophobic or have a hydrophobic/hydrophilic balance over a scale range according to their applications. For example, in some biomedical/pharmaceutical situations, water-based test fluid placed on a printed target image is required to wet the printed image surface but not spread thereon. Furthermore, the target prints may involve image and non-image regions, requiring a uniform wetting response across both regions. Thus, there is a need to develop methods and apparatus to control the surface wettability of xerographic prints.

SUMMARY

According to various embodiments, the present teachings include a method of controlling surface wettability of a xerographic print. The xerographic print can include a substrate having a toner image area on a surface of the substrate with an oil-containing layer at least partially covering the surface. An enzyme-surfactant solution including at least one hydrocarbon-degrading enzyme and at least one surfactant can then be provided and applied to the surface of the substrate to adjust a water contact angle of a treated substrate surface in a range between about 20 and about 80.

According to various embodiments, the present teachings also include a method of controlling surface wettability of a xerographic print. The xerographic print can include a substrate having a toner image area and a non-image area on a surface of the substrate with an oil-containing layer at least partially covering the surface. An enzyme-surfactant solution including at least one hydrocarbon-degrading enzyme and at least one surfactant can then be provided and applied to the surface of the substrate at a temperature ranging from about 20° C. to about 90° C. to adjust a water contact angle of a treated substrate surface in a range between about 20 and about 80. The treated substrate surface can include a treated toner image area, a treated non-image area, and a combination thereof.

According to various embodiments, the present teachings further include a method of controlling surface wettability of a xerographic print. The xerographic print can include a substrate having a toner image area and a non-image area on a surface of the substrate with a fuser oil contamination at least partially covering one or more portions of the toner image area, the non-image area, and a combination thereof. An enzyme-surfactant solution including at least one hydrocarbon-degrading enzyme and at least one surfactant can be provided and applied to the surface of the substrate for a time length ranging from about 10 ms to about 10 s to adjust a water contact angle of a treated substrate surface in a range between about 20 and about 80. The treated substrate surface can include a treated toner image area, a treated non-image area, and a combination thereof. The applied enzyme-surfactant solution can then be air-dried at room temperature to deactivate the at least one hydrocarbon-degrading enzyme and thus to deactivate the enzyme-surfactant treatment.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

It should be noted that some details of the figures have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Exemplary embodiments provide methods and apparatus of using an enzyme-surfactant solution to normalize and/or control surface wettability (e.g., hydrophobicity, hydrophilicity, and/or a balance between hydrophobicity and hydrophilicity) of an image area (e.g., with printed images) relative to a non-image area of a xerographic print or a printed substrate, where a release agent (e.g., an amine-functional silicone release agent) may or may not be applied on the xerographic print.

Figure 1:
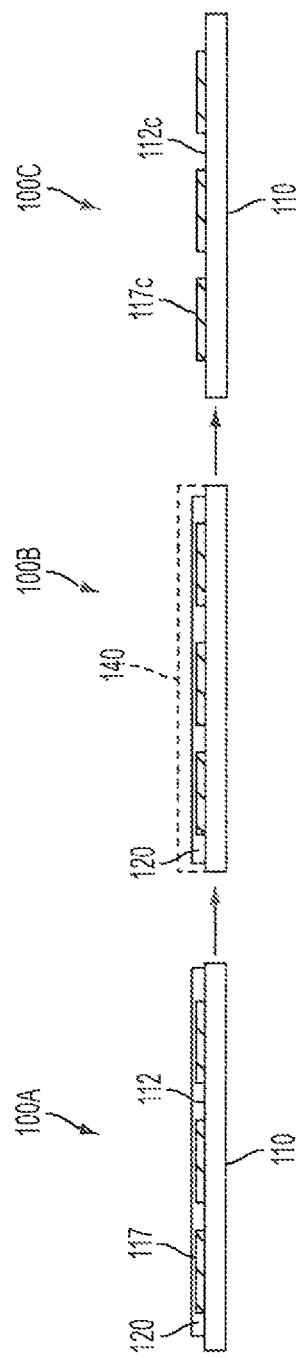
FIG. 1 depicts an exemplary method for controlling surface wettability of a xerographic print in accordance with various embodiments of the present teachings.

FIG. 1 depicts an exemplary method for controlling surface wettability of a xerographic print in accordance with various embodiments of the present teachings.

In FIG. 1, a xerographic print 100A can be provided including an image area 117 with printed images on a substrate 110 and a non-image area 112 of the substrate 110. In embodiments, the image area 117 can at least partially cover a surface of the substrate 110. For example, the image area 117 can cover a surface area of the substrate 110 between above 0 percent and less than about 100 percent leaving the rest area as the non-image area 112. Accordingly, the non-image area 112 can cover a surface area of the substrate 110 between less than about 100 percent and above 0 percent.

In embodiments, the substrate 110 can be made of a flexible or a rigid material and can be transparent or opaque. The substrate 110 can include, for example, any suitable material such as paper, wood, glass, ceramics, plastics, fabrics, textile products, polymeric films, inorganic substrates such as metals, and the like. The paper can include, for example, plain papers such as xerographic bond, writing bond, tablet, Bristol, envelope, uncoated offset, and/or lightweight opaque printing papers; coated papers such as gloss, silk and matte coated printing papers, sheet of web offset, digital coated, lightweight coated, gravure, coated SBS and recycled paperboard, and/or coated top-liner; and synthetic paper and films such as polyester, BOPP, vinyl, other polyolefin papers, and/or Teslin; and the like. The plastic films can include clear, translucent, or opaque plastics, for example, a plastic film made of polyethylene, polyethylene terephthalate, polyethylene naphthalate, polystyrene, polycarbonate, or polyethersulfone. In various embodiments, the substrate 110 can be a single layer or multi-layer.

In embodiments, the xerographic print 100A can be a print processed by an image development system or an imaging device with toner images printed on the substrate material following a fusing process. In embodiments, the fusing process can use fuser oils or release agents during fusing. As a result, the xerographic print 100A in FIG. 1 can include a layer 120 of fuser oils or release agents, referred to as an oil-containing layer 120, formed on the image area 117 and the non-image area 112 of the substrate 110. In one embodiment, the oil-containing layer 120 can be a surface hydrocarbon contamination derived from fuser oils including, for example, organopolysiloxane, amino functional, and/or mercapto functional oil compositions. Exemplary organopolysiloxane can include amino-functional silicone oils, methyl aminopropyl methyl siloxane, ethyl aminopropyl methyl siloxane, benzyl aminopropyl methyl siloxane, dodecyl aminopropyl methyl siloxane, aminopropyl methyl siloxane, and/or the like. In certain embodiments, the oil-containing layer 120 can include exemplary fuser oils/release agents of poly(dimethylsiloxane) (PDMS), amino-functionalized PDMS, mercapto-functionalized PDMS, etc.

Generally, when fuser oils/release agents are used during a fusing process, they can be applied to the fuser member to provide the release of a substrate containing an image thereon from the fuser member after the toner image has been formed on the substrate. The resulting xerographic print 100A can thus be contaminated by the oil-containing layer 120 of, e.g., amino-functionalized PDMS fuser oil. The oil-containing layer 120 can be a residual film of fuser oils/release agents with low surface energy. The oil-containing layer 120 can remain on a toner image that may cover any portion of the xerographic print. The oil-containing layer 120 can at least partially cover the toner image area and/or the non-image area of the xerographic print. The term "partially" refers to the fuser oils/release agents covering an area of the xerographic print from above 0 percent to less than 100 percent, or from about 10 percent to about 90 percent, or from about 20 percent to about 80 percent of the entire xerographic print. In embodiments, the oil amount of the oil-containing layer 120 on the substrate 110, having toner image areas 117 thereon, can range from about 1 mg/copy to about 20 mg/copy, or from about 5 mg/copy to about 16 mg/copy, or from about 9 mg/copy to about 12 mg/copy. The oil application rates of the fuser oils/release agents can be measured by, e.g., ICP (i.e., inductively coupled plasma) as known to one of ordinary skill in the art.

Referring back to FIG. 1, an enzyme-surfactant solution 140 can be provided and applied to the xerographic print 100A for a surface treatment, such that the surface wettability of the xerographic prints can be normalized and/or controlled. It is understood that the enzyme-surfactant solution 140 may be applied to specific regions encompassing image and non-image areas, only image areas or only non-image areas, and in different amounts in each region depending on the required hydrophobic/hydrophilic balance outcome.

In embodiments, the enzyme-surfactant solution 140 can be, for example, an aqueous solution including at least one enzyme, such as at least one hydrocarbon-degrading enzyme, and at least one surfactant. Suitable hydrocarbon-degrading enzymes can include lipases, oxidases, dehydrogenases, hydroxylases, oxygenases, and the like, and combinations thereof. Among them, exemplary hydrocarbon-degrading enzymes can include monooxygenases, dioxygenases, monomethanoxygenases, alcohol dehydrogenases, aldehyde dehydrogenases, acetaldehyde dehydrogenases, paraffin hydroxylases, hydrolase-aldolases, and the like, and combinations thereof. The hydrocarbon-degrading enzymes can break down hydrocarbons into short-chain fatty acids that can be more easily solubilized and removed from the substrate surface. In embodiments, other enzymes, such as proteases, amylases, cellulases, and the like, and mixtures thereof, can be present with the hydrocarbon-degrading enzymes in the enzyme-surfactant solution 140.

In an embodiment, the hydrocarbon-degrading enzymes can be extracted and isolated from microorganisms and incorporated into the enzyme-surfactant solution as a powder or aqueous solution. In another embodiment, the hydrocarbon-degrading enzymes can be secreted by live microorganisms present in the enzyme-surfactant solution.

Suitable microorganisms can include Gram-positive and Gram-negative bacteria, including endospores thereof; fungi; yeast; and combinations thereof. Exemplary bacteria can include *Acetobacter* spp., *Anthrobacter* spp., *Acinetobacter* spp., *Actinomyces* spp., *Alcaligenes* spp., *Bacillus* spp., *Beneckea* spp., *Corynebacterium* spp., *Flavobacterium* spp., *Mycobacterium* spp., *Nocardia* spp., *Pseudomonas* spp., *Rhadococcus* spp., *Xanthomonas* spp., and the like, and combinations thereof; preferably, *Pseudomonas* spp., *Anthrobacter* spp., *Rhadococcus* spp., and combinations thereof. Exemplary yeast can include *Candida* spp., *Crytococcus* spp., *Debaryomyces* spp., *Hansenula* spp., *Pichia* spp., *Rhodotorula* spp., *Sporobolomyces* spp., *Torulopsis* spp., *Trichosporon* spp., and the like, and combinations thereof; preferably *Candida* spp. Exemplary fungi can include *Aspergillus* spp., *Cladosporium* spp., *Corollaspora* spp., *Dendryphiella* spp., *Gliocladium* spp., *Lulworthia* spp., *Penicillium* spp., *Varicospora* spp., and the like, and combinations thereof; preferably, *Aspergillus* spp., *Penicillium* spp., and combinations thereof. The microorganisms can naturally express hydrocarbon-degrading enzymes or be genetically modified to express hydrocarbon-degrading enzymes in greater quantity than native, non-genetically-modified microorganisms. Commercially available concentrated enzyme solutions can include EATOILS™ products, such as BT200™, by World-Ware Enterprises Ltd. of Ontario, Canada.

In embodiments, the enzyme-surfactant solution 140 can further include at least one surfactant. Exemplary surfactants can include alkylphenol ethoxylates, alkaline metal salts of alkane sulfonic acid, alkanolamines, and mixtures thereof. The surfactants can solubilize short-chain fatty acids produced by the above enzymes as a result of hydrocarbon degradation, and remove the short-chain fatty acids from the substrate surface.

Suitable alkylphenol ethoxylates can have the general formula $RC_6H_4(OCH_2CH_2)_xOH$, wherein R can be a long chain aliphatic group including from about 7 to about 60, or from about 10 to about 40, or from about 20 to about 30 carbon atoms, and x can range from about 1 to about 12, or from about 5 to about 10, for example, from about 7 to about 10. The R group can be either straight or branched, such as nonyl or octyl, and can be attached to various positions on the aromatic ring structure. In an embodiment, both a relatively low molecular weight alkylphenol ethoxylate (e.g., x can range from about 1 to about 6) and a relatively high molecular weight alkylphenol ethoxylate (e.g., x can range from about 8 to about 12) can be used. While not intended to be limited by any theory, it is believed that the lower molecular weight alkylphenol ethoxylate can assist in the removal and/or solubilization of higher molecular weight hydrocarbons and that the higher molecular weight alkylphenol ethoxylate can assist in the removal and/or solubilization of lower molecular weight hydrocarbons.

Suitable alkaline metal salts of alkane sulfonic acid can have the general formula $RSO_3^-M^+$ and $ArSO_3^-M^+$, wherein R is a long chain aliphatic group including from about 7 to about 60, or from about 10 to about 40, or from about 20 to about 30 carbon atoms, Ar is a substituted or unsubstituted aromatic group, and $M^+$ is an alkaline metal cation, such as sodium and potassium. Suitable $RSO_3^-$ and $ArSO_3^-$ anions can include, for example, olefin sulfonates, aliphatic sulfonates, benzenesulfonates, toluenesulfonates, dodecylbenzenesulfonates, and the like. While not intending to be limited by any theory, it is believed that alkaline metal salts of alkane sulfonic acid can provide detergency and help prevent re-adherence of hydrocarbons to the substrate surface after removal. Exemplary alkaline metal salts of alkane sulfonic acid can include sodium salts of substituted benzenesulfonate such as p-toluenesulfonate, dodecylbenzenesulfonate, and the like, or primary alkane sulfonate, and combinations thereof.

Suitable alkanolamines can have the general formula: $(HO(CH_2)_z)_{3-y}NH_y$, wherein z ranges from about 2 to about 20, or from about 2 to about 10, or from about 2 to about 6, and y is 0, 1, or 2. Exemplary alkanolamines can include trialkanolamines of the formula $(HO(CH_2)_z)_3NH$, wherein z ranges from about 2 to about 6. In an embodiment, the alkanolamine can be triethanolamine. While not intended to be limited by any theory, it is believed that, like alkaline metal salts of alkane sulfonic acid, the alkanolamines can provide detergency and help prevent re-adherence of hydrocarbons to the substrate surface after removal.

In an embodiment, the enzyme-surfactant solution 140 can be provided as a concentrate and diluted with water to produce the enzyme treatment. The enzyme-surfactant solution 140 applied to the xerographic print 100A can include at least one enzyme in an amount ranging from about 1% to about 85% by weight, for example from about 3% to about 65% by weight, or from about 5% to about 45% by weight, or from about 5% to about 25% by weight of the total enzyme-surfactant solution 140.

In various embodiments, the enzyme-surfactant solution 140 can be applied, uniformly or following specific patterns, in accordance with the general understanding of 'flood' or 'spot' coating as it is understood in the printing industry, to the xerographic print 100A. In one embodiment, offset gravure or anilox flexo coating, as known to one of ordinary skill in the art, can be employed to apply the enzyme-surfactant solution 140 to the printed image either flood or spot. The Epic CTi-635 coater, designed to provide in-line anilox flexo coating for Xerox iGen printing can be one such coater. Another embodiment can use ink-jet technology, thermal or piezo, to apply the enzyme-surfactant solution 140, which provides precise placement of the enzyme-surfactant solution 140 with respect to the printed image or for variable data format requirements. Other coating techniques can include spray coating, air-knife, rod and multi-roll coating, knife-on-roll coating and the like.

In embodiments, depending on selections and amount of both the enzymes and the surfactants and also depending on the materials and areas to be treated, the treatment of the enzyme-surfactant solution 140 can be performed at a temperature ranging from about 20° C. to about 90° C., or from about 20° C. to about 40° C., or from about 20° C. to about 30° C. The treatment of the enzyme-surfactant solution 140 can be performed for a time length ranging from about 10 ms to about 10 s, or from about 20 ms to about 5 s, or from about 20 ms to about 2 s.

Following the enzyme-surfactant treatment, the enzyme-surfactant applied substrate 100B in FIG. 1 can be air-dried at room temperature for a time length and/or heated to a temperature to denature the enzymes used in the enzyme-surfactant solution 140, resulting in loss or deactivation of enzymatic activity and thus treatment completion.

For example, the enzyme-surfactant applied substrate 1008 can be air-dried at room temperature to deactivate the enzymatic activity, e.g., for more than about 1 second, such as from about 1 second to about 35 seconds, or from about 10 seconds to about 30 seconds, or from about 15 seconds to about 25 seconds. While not intended to be limited by any theory, it is believed that the total drying time at room temperature can be an indicator of how fast the enzymes can degrade the fuser oil, with a shorter drying time being associated with faster enzymatic activity.

In another example, the enzyme-surfactant applied substrate 1008 can be heated, e.g., passed through heated fuser members, to deactivate the enzymatic activity, e.g., at a temperature ranging from about 140° C. to about 200° C., such as from about 150° C. to about 190° C., for example at about 180° C.

In embodiments, the air-drying process at room temperature and the heating process to a temperature can be combined to deactivate the enzymatic activity and to complete the enzyme-surfactant treatment. Optionally, following the deactivation process by drying and/or heating, an optional washing, rinsing, and/or cleaning process can be performed to remove any residues left behind on a treated substrate 100C.

In embodiments, the treatment of the enzyme-surfactant solution 140 to the xerographic print 100A, including the oil-containing layer 120 at least partially covering the image area 117 and/or the non-image area 112, can generate the treated substrate 100C having a treated image area 117c and a treated non-image area 112c. In one embodiment, the oil-containing layer 120 can include PDMS amino oil. In embodiments, the treatment of the enzyme-surfactant solution 140 can, for example, (1) remove the oil-containing layer 120 from the xerographic print (see 100A), e.g., by using suitable surfactant to solubilize the layer 120; and (2) control or improve surface wettability of the treated substrate 100C having the treated image area 117c and the treated non-image area 112c. Specifically, the solubilized oil-containing layer 120 can be degraded by the enzyme in the enzyme-surfactant solution 140. Oil molecules of the oil-containing layer 120 can be broken down into short chain fatty acids. The enzymes can also facilitate solubilizing the oil-containing layer 120 from the xerographic print 100A.

As a result, the treated substrate 100C can have a treated substrate surface including one or more portions of the treated image area 117c and/or the treated non-image area 112c. The treated substrate surface can have a water contact angle ranging from about 20 to about 80, or from about 30 to about 70, or from about 50 to about 70. While in many embodiments, the water contact angle of the treated toner image area 117c can match (e.g., be the same as) that of the treated non-image area 112c of the treated substrate 100C, the water contact angle of the treated toner image area 117c and the treated non-image area 112c can also be controlled having two different levels, by adjusting the enzyme-surfactant treatment.

In embodiments, the water contact angle can be adjusted or controlled without limitation by varying the dilution ratio of the enzyme-surfactant solution and its drying and/or heating process, the selection/amount of enzymes and surfactants, etc.

Figure 2:
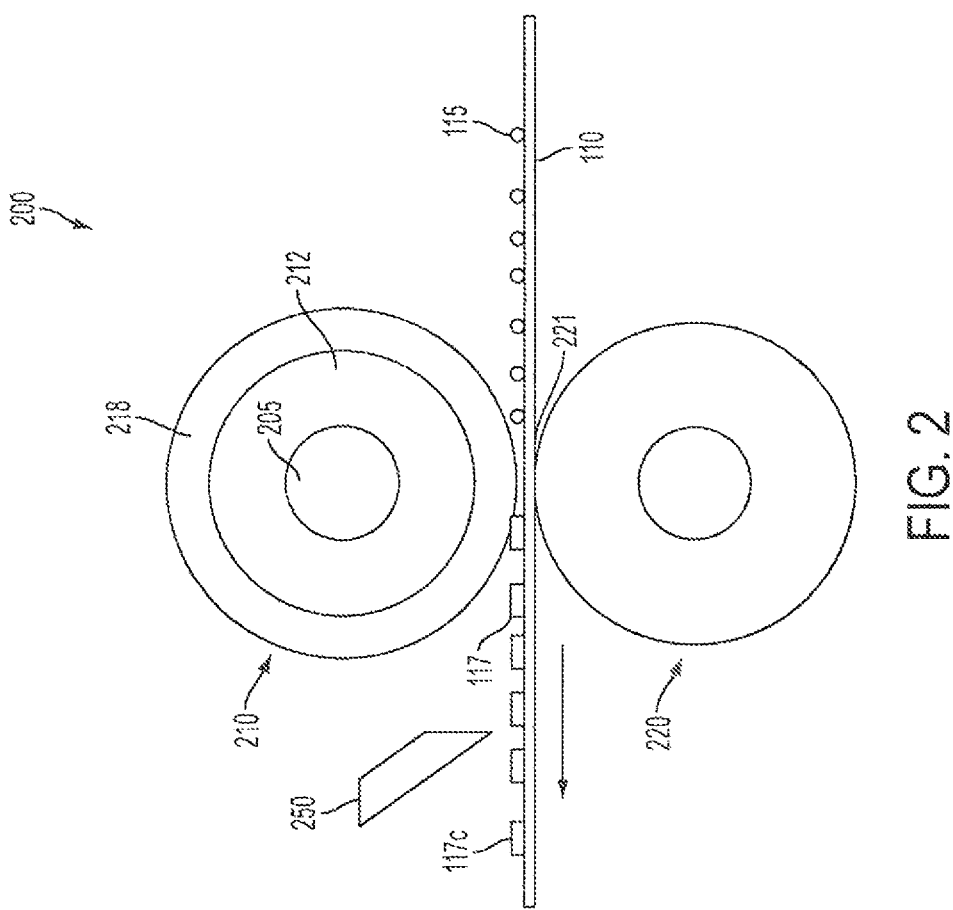
FIG. 2 depicts an exemplary fusing apparatus in accordance with various embodiments of the present teachings.

Various embodiments can also include a fusing apparatus as depicted in FIG. 2. The exemplary fusing apparatus 200 can include a fuser belt or fuser roll 210 having one or more functional layers 218 over a suitable roll substrate 212. The roll substrate 212 can be, for example, a hollow cylinder fabricated from any suitable metal. The fuser roll 210 can further have a suitable heating element 205 disposed in the hollow portion of the substrate 212, which is coextensive with the cylinder. Backup or pressure roll 220, as known to one of ordinary skill in the art, can cooperate with the fuser roll 210 to form a nip or contact arc 221 through which a substrate 110 such as a polyester substrate or other suitable substrate passes, such that toner images 115 on the substrate 110 contact the fuser roll 210 for fusing/fixing. The fusing process can be performed at a temperature ranging from about 140° C. to about 200° C., such as from about 150° C. to about 190° C., for example at about 180° C. Optionally, a pressure can be applied during the fusing process by the backup or pressure roll 220.

Following the fusing process, after the substrate 110 passes through the contact nip 221, fused toner images 117 can be formed on the substrate 110. In embodiments, thin liquid films of fuser oils/release agents can be applied to ensure release between the fuser roll surface and the fused toner images 117 in the diverging roll nip exit, leaving a barrier of fuser oil on the fuser roll 210 and/or the surfaces of substrate 110 having the fused toner images 117 thereon. After exiting the contact nip 221, the substrate 110 having the fused toner images 117 thereon can then be treated by an enzyme-surfactant application unit 250 for applying an aqueous enzyme-surfactant solution thereto. Following the treatment of the enzyme-surfactant solution on the substrate surfaces that have oil-containing layer thereon, the applied aqueous enzyme-surfactant solution can be air-dried at room temperature for a time length and/or heated, e.g., through a second fuser unit including, e.g., a second fuser roll and/or a second backup roll, to deactivate the treatment. For example, the treated substrate 100C can be passed through heated fuser rolls (see 210 and 220) at a roll speed of about 600 to about 2000 rpm, or from about 650 to about 1500 rpm, or from about 700 to about 1400 rpm. In embodiments, a heating unit including, e.g., a second fuser unit or an oven unit, can be configured, e.g., within the enzyme-surfactant application unit 250. Both the heating unit and/or the enzyme-surfactant application unit 250 can be considered as an extension to a conventional printing unit following the conventional fusing apparatus. Heating the enzyme-treated substrate to a temperature of 140° C. and above can denature the hydrocarbon-degrading enzymes and halt the enzymatic activity. A treated substrate 100C can then be provided with desired surface wettability.

Although for illustrative purposes the description herein primarily relates to the enzyme-surfactant treatments for xerographic prints, one of ordinary skill in the art will understand that the enzyme-surfactant treatments can be used for any types of marked materials. For example, a marked material including solid ink images thereon can be treated by the disclosed enzyme-surfactant solution to form a treated surface, e.g., a treated ink-image surface and/or a treated non-image surface, with a desired water contact angle. The water contact angle can range from about 20 to about 80, or from about 30 to about 70, or from about 50 to about 70.

EXAMPLES

Selected enzyme/surfactant materials were diluted with water to various levels to form an enzyme-surfactant solution, which was then applied as a liquid film coating over the printed substrate using a Paasche airbrush spray applicator. The coated films were allowed to air-dry. Print images were made using a DC8000 and an iGen3 thereby including two toners, two amino-PDMS fuser oils, and two different fuser oil rates and fusers. Two exemplary synthetic materials of a 11 mil polyester and a 10 mil BOPP (bi-axially oriented polypropylene) were used as a substrate to receive images. To evaluate the effectiveness of the treatment at modifying the surface wettability of the printed images, contact angle of DI water of the samples (i.e., the printed substrates) was measured as a function of time on a sessile drop using a contact angle goniometer supplied by First Ten Angstroms, Inc. (Portsmouth, Va.), as shown in FIG. 3.

Figure 3:
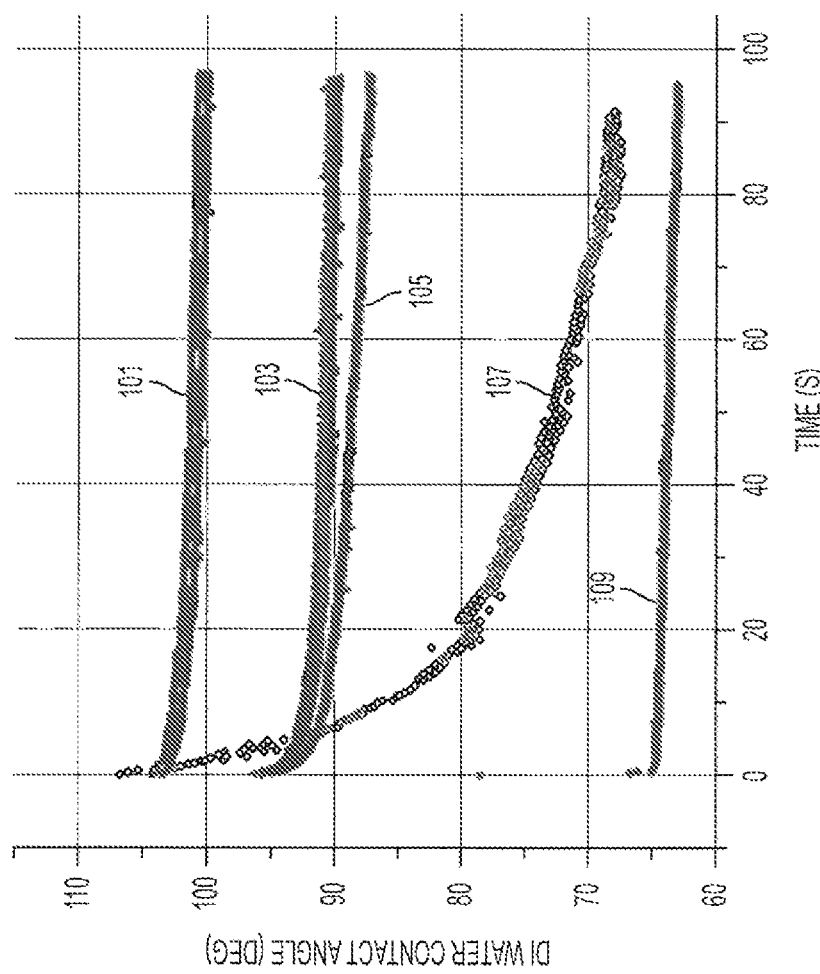
FIG. 3 compares the water contact angle of a xerographic print after different surface treatments in accordance with various embodiments of the present teachings.

FIG. 3 depicts initial hydrophobicity of a black fuser toner image on polyester substrate (see 101); improvement in wetting achieved by exposure print surface to UV ozone (see 103); wetting achieved by removing the fuser oil on the print surface by wiping with hexane (see 105); and water contact response on the polyester film surface, i.e., non-image area, but contaminated by fuser oil (see 107). The contact angle response (see 109 of FIG. 3) of an image area on the polyester film surface from an oil-containing fusing, following a treatment of an enzyme-surfactant solution, shows a very rapid stable value at about 65°. As compared, the hydrophobic/hydrophilic balance achieved in this example was different than that achieved by removing the fuser oil alone using conventional treating methods involving UV ozone or hexane.

Figure 4A:
FIGS. 4A-4B depict water contact angle illustrations of a black image surface before and after an enzyme-surfactant treatment in accordance with various embodiments of the present teachings.
Figure 4B:
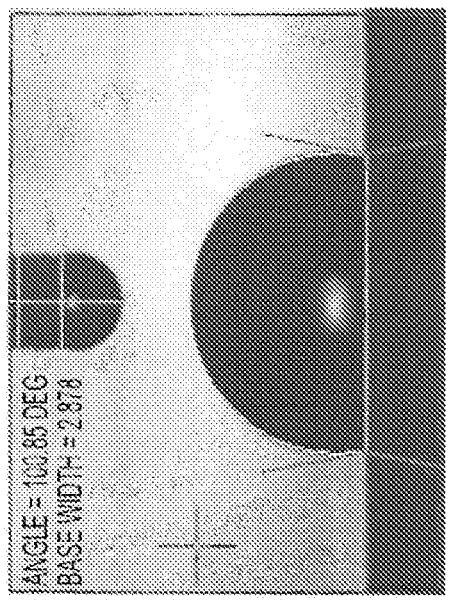

FIG. 4A depicts an exemplary water contact angle illustration on black image area of iGen3 print on 11 mil polyester substrate, showing a hydrophobic surface. FIG. 4B depicts an exemplary water contact angle illustration after a treatment of the enzyme-surfactant solution on the black image area of iGen3 print on 11 mil polyester substrate, showing a surface with desirable hydrophobic/hydrophilic balance.

Table 1 compares water contact angle results of a printed black image on a substrate of 11 mil polyester after different treating methods. As shown, the treatment of the disclosed enzyme-surfactant solution can adjust or reduce water contact angle to achieve a desired surface hydrophobic/hydrophilic balance.

TABLE 1

|  | Black Image | Hexane Kim wipes | Ozone 30s | Ozone 60s | Paasche Water | Paasche 25% enzyme | Paasche 10% enzyme | Paasche 5% enzyme |
|---|---|---|---|---|---|---|---|---|
| iGen DC 8000 | 100.85 96.75 | 87.66 | 95.59 | 89.88 | 96.94 | <20 | 63.26 <20 | 57.57 66.06 |

Table 2 lists water contact angle results of a printed black image along with related non-image area on a substrate of 11 mil polyester before and after the disclosed enzyme-surfactant treatment. As shown, the treatment of the disclosed enzyme-surfactant solution can adjust or reduce water contact angle for a desired surface hydrophobic/hydrophilic balance of the image area and the non-image area. The image area and the non-image area can have different water contact angles.

TABLE 2

| Prints | | Paasche 10% enzyme | | Paasche 5% enzyme | |
|---|---|---|---|---|---|
| Black image | Non-image | Black image | Non-image | Black image | Non-image |
| 100.85 | 68.52 | 63.26 | | 57.57 | |
| 96.75 | 64.48 | <20 | <20 | 66.06 | <30 |

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:

1. A method of removing oil from and controlling surface wettability of a xerographic print comprising:

providing a substrate comprising a toner image area on a surface of the substrate and an oil-containing layer at least partially covering the surface;

providing an enzyme-surfactant solution comprising at least one hydrocarbon-degrading enzyme and at least one surfactant; and applying the enzyme-surfactant solution to the surface of the substrate comprising the oil-containing layer to form a treated substrate surface with a water contact angle ranging from about 20° to about 80°, wherein the substrate is treated by the applied enzyme-surfactant solution for a time length ranging from about 10 ms to about 10 s, wherein the treated substrate surface comprises a treated toner image area, and wherein the toner image area comprises toner before and after the enzyme-surfactant solution is applied to the surface of the substrate, and wherein the at least one surfactant is selected from the group consisting of alkylphenol ethoxylates, alkaline metal salts of alkane sulfonic acid, alkanolamines, and mixtures thereof.

2. The method of claim 1, wherein the treated substrate surface has a water contact angle ranging from about 30° to about 70°.

3. The method of claim 1, wherein the treated substrate surface further comprises a treated area without a toner image and wherein the treated toner image area and the treated area without a toner image have a same or a different water contact angle ranging from about 20° to about 80°.

4. The method of claim 1, wherein the substrate is treated by the enzyme-surfactant solution at a temperature ranging from about 20° C. to about 90° C. for a time length ranging from about 20 ms to about 5 s.

5. The method of claim 1, further comprising deactivating the at least one hydrocarbon-degrading enzyme of the enzyme-surfactant solution after treating the surface of the substrate.

6. The method of claim 5, further comprising air-drying the enzyme-surfactant solution at room temperature for a time length ranging from about 1 second to about 35 seconds.

7. The method of claim 5, further comprising deactivating the applied enzyme-surfactant solution by heating the substrate at a temperature ranging from about 140° C. to about 200° C.

8. The method of claim 1, wherein the oil-containing layer covers the surface of the substrate from above about 0 percent to less than about 100 percent to provide a covered surface area, and wherein the covered surface area comprises one or more portions of the toner image area, an area without a toner image, or a combination thereof on the surface of the substrate.

9. The method of claim 1, wherein the oil-containing layer covers the surface of the substrate ranging from about 1 mg/copy to about 20 mg/copy.

10. The method of claim 1, wherein the oil-containing layer comprises organopolysiloxane, poly(dimethylsiloxane) (PDMS), amino-functionalized PDMS, or mercapto-functionalized PDMS.

11. The method of claim 1, wherein the at least one hydrocarbon-degrading enzyme is present in an amount ranging from about 1% to about 85% by weight of the enzyme-surfactant solution.

12. The method of claim 1, wherein the at least one hydrocarbon-degrading enzyme is present in an amount ranging from about 5% to about 25% by weight of the enzyme-surfactant solution.

13. The method of claim 1, wherein the substrate is formed of paper, wood, glass, plastics, rubbers, ceramics, fabrics, metals, or combinations thereof, and wherein the plastics comprise polyester or polypropylene.

14. The method of claim 1, wherein the at least one hydrocarbon-degrading enzyme is selected from the group consisting of lipases, oxidases, dehydrogenases, hydroxylases, oxygenases, and combinations thereof.

15. The method of claim 1, wherein the at least one hydrocarbon-degrading enzyme is selected from the group consisting of lipases, monooxygenases, dioxygenases, monomethanoxygenases, alcohol dehydrogenases, aldehyde dehydrogenases, acetaldehyde dehydrogenases, paraffin hydroxylases, hydrolase-aldolases, and combinations thereof.

16. The method of claim 1, wherein the at least one hydrocarbon-degrading enzyme is secreted from a microorganism selected from the group consisting of Gram-positive bacteria, Gram-negative bacteria, fungi, yeast, and combinations thereof.

17. A method of removing oil from and controlling surface wettability of a xerographic print comprising:
providing a substrate comprising a toner image area and an area without a toner image on a surface of the substrate, and an oil-containing layer at least partially covering the surface;
providing an enzyme-surfactant solution comprising at least one hydrocarbon-degrading enzyme and at least one surfactant; and
applying the enzyme-surfactant solution to the surface of the substrate comprising the oil-containing layer at a temperature ranging from about 20° C. to about 90° C. to provide a treated substrate surface with a water contact angle ranging from about 20° to about 80°,
wherein the substrate is treated by the applied enzyme-surfactant solution for a time length ranging from about 10 ms to about 10 s,
wherein the treated substrate surface comprises a treated toner image area, a treated area without a toner image, or a combination thereof, and wherein the toner image area comprises toner before and after the enzyme-surfactant solution is applied to the surface of the substrate, and wherein the at least one surfactant is selected from the group consisting of alkylphenol ethoxylates, alkaline metal salts of alkane sulfonic acid, alkanolamines, and mixtures thereof.

18. The method of claim 17, further comprising deactivating the enzyme-surfactant solution by heating the substrate at a temperature ranging from about 140° C. to about 200° C.

19. A method of removing fuser oil contamination from and controlling surface wettability of a xerographic print comprising:
providing a substrate comprising a toner image area and an area without a toner image, and a fuser oil contamination at least partially covering one or more portions of the toner image area, the area without a toner image, or a combination thereof;
providing an enzyme-surfactant solution comprising at least one hydrocarbon-degrading enzyme and at least one surfactant;
applying the enzyme-surfactant solution to the surface of the substrate comprising the fuser oil contamination for a time length ranging from about 10 ms to about 10 s to provide a treated substrate surface with a water contact angle ranging from about 20° to about 80°, wherein the treated substrate surface comprises a treated toner image area, a treated area without a toner image, or a combination thereof; and
air-drying the enzyme-surfactant solution to deactivate the at least one hydrocarbon-degrading enzyme; and
wherein the toner image area comprises toner before the enzyme-surfactant solution is applied to the surface of the substrate and after the enzyme-surfactant solution is air-dried, and wherein the at least one surfactant is selected from the group consisting of alkylphenol ethoxylates, alkaline metal salts of alkane sulfonic acid, alkanolamines, and mixtures thereof.

* * * * *